(12) United States Patent
von der Haar

(10) Patent No.: US 6,870,898 B1
(45) Date of Patent: Mar. 22, 2005

(54) COMPUTED TOMOGRAPHY APPARATUS WITH AUTOMATIC PARAMETER MODIFICATION TO PREVENT IMPERMISSIBLE OPERATING STATES

(75) Inventor: Thomas von der Haar, Nürnberg (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/009,859

(22) PCT Filed: Apr. 25, 2000

(86) PCT No.: PCT/DE00/01276

§ 371 (c)(1),
(2), (4) Date: Oct. 24, 2001

(87) PCT Pub. No.: WO00/67006

PCT Pub. Date: Nov. 9, 2000

(30) Foreign Application Priority Data

Apr. 28, 1999 (DE) .......................... 199 19 423

(51) Int. Cl.⁷ ................................. H05G 1/42
(52) U.S. Cl. ...................................... 378/97
(58) Field of Search .................... 378/97, 108, 111, 378/115, 116, 8, 62, 4, 162, 901; 345/1, 156, 326

(56) References Cited

U.S. PATENT DOCUMENTS 4,119,856 A   10/1978   Franke
4,160,906 A   7/1979   Daniels et al.
5,828,719 A   10/1998   He et al.
6,178,228 B1   1/2001   Schol

FOREIGN PATENT DOCUMENTS

DE   OS 198 10 069   12/1999
EP   0 809 422   11/1997

OTHER PUBLICATIONS

Patent Abstracts of Japan, vol. 005, No. 117 (E–067) for Japanese Application 56054796, (no date).

10 Jahre Computertomographic—ein Rückblick, Dümmling, electromedia 52, No. 1 (1984) pp. 13–28, (no date).

*Primary Examiner*—William Oen
(74) *Attorney, Agent, or Firm*—Schiff Hardin LLP

(57) ABSTRACT

A computed tomography (CT) device has adjustable operational parameters and a control unit and a unit for preselecting a combination of operational parameters for an examination to be carried out. The control unit determines, for the case where a combination of operational parameters which might lead to an impermissible operating state is preselected for an examination to be carried out, a value for at least one operational parameter which deviates from the preselected combination of operational parameters and for which the planned examination can be carried out in a manner avoiding the impermissible operating state without a significant reduction in the image quality by comparison with the preselected combination of operational parameters.

27 Claims, 3 Drawing Sheets

COMPUTED TOMOGRAPHY APPARATUS WITH AUTOMATIC PARAMETER MODIFICATION TO PREVENT IMPERMISSIBLE OPERATING STATES

BACKGROUND OF THE INVENTION

1. Field of the Invention

The present invention relates to a CT device of the type having adjustable operational parameters, and a control unit, connected to an input unit for preselecting a combination of operational parameters for an examination to be carried out.

2. Description of the Prior Art

During examinations with a computed tomography apparatus, it can occur that examinations cannot be carried out with a combination of operational parameters that is desired by the user, on account of technical or user-defined limitations of the permissible values of the operational parameters of the CT device. In particular, the thermal loading capacity of the X-ray source—generally embodied as an X-ray tube—of the CT device has a limiting effect on specific operational parameters (e.g. scan time, i.e. that period of time during which an object under examination is irradiated with X-rays in order to carry out an examination, scan length, i.e. that extent of the object under examination in the direction of the system axis over which an object under examination is scanned with X-rays in order to carry out an examination, tube current, tube voltage, etc.).

European Application 0 809 422 describes a method for establishing and/or correcting exposure errors in X-ray radiographs, in which, during the recording of an X-ray image, a check is made to determine whether the actual exposure rate corresponds to a predicted exposure rate. If this is not the case, the recording is terminated or suitable recording parameters are corrected with the aim of achieving a correct exposure.

SUMMARY OF THE INVENTION

An object of the present invention is to design a CT device of the type described above wherein a user is provided with a control aid for those examinations for which the user has set a combination of operational parameters which is not at least within the technical limits with regard to the individual operational parameters.

The above object is achieved in accordance with the invention in a computed tomography (CT) device which has adjustable operational parameters and a control unit and a unit for preselecting a combination of operational parameters for an examination to be carried out. The control unit determines, for the case where a combination of operational parameters which might lead to an impermissible operating state is preselected for an examination to be carried out, a value for at least one operational parameter which deviates from the preselected combination of operational parameters and for which the planned examination can be carried out in a manner avoiding the impermissible operating state without a significant reduction in the image quality by comparison with the preselected combination of operational parameters.

Thus, the CT device according to the invention affords a possibility of resolving conflicts for those combinations of operational parameters which do not lie within the technical limits of the CT device and/or within user-defined limit values, with the consequence that the corresponding examination could not actually be carried out. This is because in the case of the CT device according to the invention, a modified value is determined for at least one operational parameter of the preselected combination, which has been changed such that the image quality, in particular the image noise, is maintained as far as possible in comparison with the initially set combination of operational parameters, and so that the CT device is operated within the permissible technical or user-defined limits. The user thus is enabled by this control aid to carry out an examination which substantially corresponds to the originally intended examination, but which can be carried out without technical limits of the CT device and/or user-defined limit values being exceeded. As used herein "exceed" is not used in the literal sense but rather to mean that a limit value is transgressed, i.e. an upper limit value is exceeded or a lower limit value is undershot.

Of course the changes to the operational parameters which are specified by the control unit are possible only within the technical limits of the CT device. Technical limits Include, inter alia: maximum and minimum tube current that can be set, maximum and minimum possible scan time, maximum and minimum pitch that can be set, i.e. the advance in the direction of the system axis per revolution of the radiation source relative to the collimated width of a linear array of detector elements of the detector (collimated layer thickness), etc.

In order to bring about a combination of operational parameters which does not represent an impermissible operating state, the control unit can change one or a number of operational parameters of the chosen combination of operational parameters.

The changes to the operational parameters which are specified by the control unit can either be set automatically (with or without corresponding information of the user) or be presented to the user as a proposal, in the latter case the actual setting of a deviating operational parameter being effected only in response to corresponding enabling by the user. The first-mentioned embodiment, whether with or without information of the user, is advantageous when marginal changes in one or a number of operational parameters are sufficient. By contrast, if relatively large changes are necessary, in particular those which have an effect in the sense of impairing the expected image quality, then the last-mentioned embodiment, which provides for enabling by the user, is advantageous. In this case, the CT device has a unit which determines whether an automatic change can be effected or whether enabling by the user is required, depending on the operational parameter affected in each case and on the extent of the required change, for example on the basis of a table which contains the corresponding information and is stored in the CT device.

In a preferred embodiment of the invention, the CT device according to the invention is provided for carrying out spiral scans in which an X-ray source rotates around an object under examination and, at the same time, a translational relative movement is effected between the object under examination, and the X-ray source and also a detector. The spiral scan is carried out during a scan time during which the X-ray source is operated with a tube current. The control unit, in the case of an impermissible preselected combination of operational parameters, in order to avoid an impermissible operating state, specifies a value for at least one operational parameter which derived using the specified value for that operational parameter, so that the product of tube current and scan time (mAs product) is not significantly reduced by comparison with the preselected combination of operational parameters.

It is ensured that the mAs product used for carrying out the envisaged examination is not significantly reduced by the change in the operational parameters. Since the mAs product, which contributes to a reconstructed sectional image (CT image), is crucial to the image noise and hence the image quality (the image noise increases as the mAs product decreases), it is ensured that despite the changed operational parameters, no considerable change in the image quality occurs.

For the 180LI or 360LI interpolation which is typically used in the reconstruction of sectional images from spiral scans and is described in the literature, it is difficult to comply with this condition. In these types of interpolation, the layer sensitivity profile is dependent on the pitch, while the mAs product is independent of the pitch. Thus, in an embodiment of the invention an electronic computing device for the reconstruction of sectional images is provided which reconstructs the sectional images in such a way that the slice sensitivity profile of a reconstructed sectional image is at least essentially independent of the pitch, while the mAs product serving for obtaining the data on which a sectional image is in each case based depends on the pitch. In this case, the mAs product, which contributes to a reconstructed sectional image, is proportional to the product of tube current and scan time, with the consequence that the image noise only depends on the product of tube current and scan time if no other operational parameters are changed. The requirement that no reduction in the image quality is supposed to occur as a result of the specified changes to operational parameters can then be met, in an embodiment of the invention, by the fact that the product of tube current and scan time in the operational parameters prescribed by the control unit is equal to the product of tube current and scan time in the desired combination of operational parameters. This procedure encounters its limits, however, in the case of large pitch values p (guide value p>1.5*n, where n=1 in the case of a CT device with a detector system having a single linear array of detector elements, and corresponds to the number of simultaneously recorded slices in the case of a CT device with a detector system having a number of linear arrays of detector elements), since image artifacts increase appreciably in that case.

As already mentioned, within the technical limits of the device, the user can additionally set upper or lower limit values for operational parameters within which the changes to the operational parameters which are specified by the control unit must fall. Thus, it is possible to define e.g. a maximum permissible scan time in order to be able to carry out a scan, i.e. an examination, e.g. within a time of holding one's breath. Equally it is possible to define a maximum permissible pitch in order e.g. to limit the intensity of the artifacts in the reconstructed sectional images. Furthermore, it is possible to define a minimum pitch in order, for example, to prevent a specific temporal resolution from being undershot.

In a further embodiment of the invention, operational parameters can be changed while taking account of an optimization goal, in which case, if a number of optimization aims are present, it is possible to prescribe a rank order of the optimization goals. The optimization goals may be, for example, minimum scan time, maximum spatial resolution, maximum temporal resolution, maximum scan length.

It may occur, on the basis of the preselected combination of operational parameters, while complying with the limit values, it is not possible to determine a combination of operational parameters which represents a permissible operating state, so it is unavoidable for at least one limit value to be exceeded. For this case, in the embodiment of the invention the control unit offers for selection at least one combination of operational parameters which, with at least one limit value not being complied with, is approximated to the preselected combination of operational parameters without an impermissible operating state being present. In this connection, the control unit can offer a number of combinations of operational parameters which are based on various optimization goals, so the user can choose a permissible combination of operational parameters for which one or a number of limit values is or are exceeded in the sense of an optimization goal of the examination. Embodiments of the invention may provide for the control unit to automatically set a value of the corresponding operational parameter which exceeds a limit value, if appropriate with the user being informed, and to carry out the planned examination, or to inform the user about a value of the corresponding operational parameter which exceeds a limit value and to carry out the envisaged examination only when the user enables the performance of the envisaged examination. This last embodiment is expedient principally in those cases in which not complying with the limit value might lead to a reduction in the image quality compared with the image quality which would be achieved in the case of the preselected combination of operational parameters.

In another embodiment the control unit offers combinations of operational parameters for successive examinations of the same object under examination while taking account of various optimization goals. It is then possible, for example, to carry out an examination with maximum spatial resolution and then an examination with maximum temporal resolution, in succession.

In a further embodiment of the invention a unit for entering a rank order of the operational parameters is provided, and the control unit complies with the rank order of the operational parameters in the event of operational parameters being changed to values which deviate from values of a preselected combination of operational parameters. This means an attempt is made to realize a permissible combination of operational parameters first by changing the operational parameter which is in first place in the rank order. If this is unsuccessful, then the control unit seeks to bring about a permissible combination of operational parameters by changing the operational parameter which is in second place in the rank order, etc. It is thus possible to prescribe a rank order which ensures that the values of specific operational parameters deemed by a user to be particularly significant for the intended examination are changed only when this is unavoidable, by the corresponding operational parameters being placed as far down as possible on the priority list.

DESCRIPTION OF THE PREFERRED EMBODIMENTS

Figure 1:
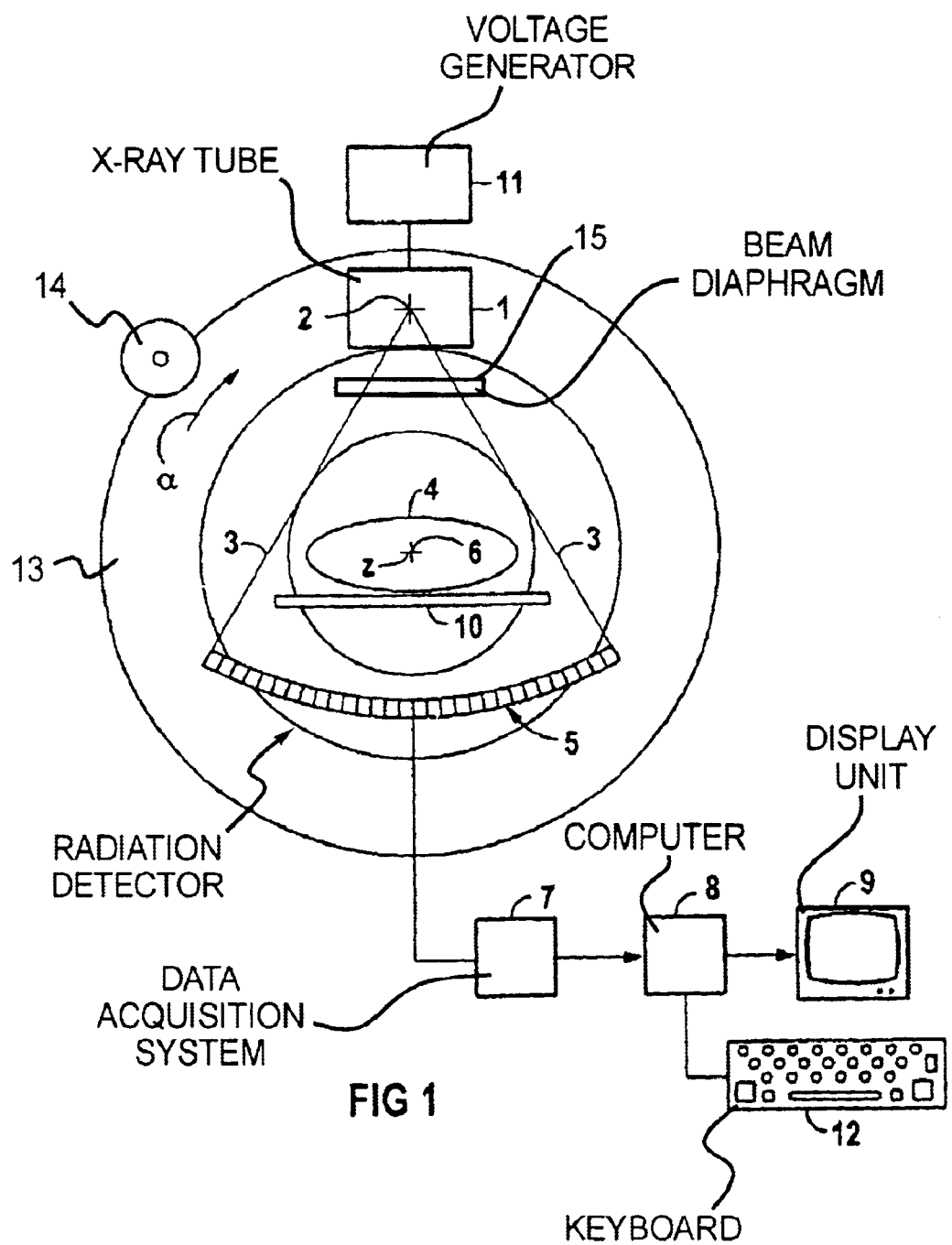
FIG. 1 is a schematic illustration of a computed tomography apparatus constructed and operating in accordance with the principles of the present invention.

A CT device according to the invention is illustrated schematically in FIG. 1, this device having an X-ray source 1, e.g. an X-ray tube, with a focus 2, from which a fan-shaped X-ray beam 3 is emitted which proceeds through a diaphragm (not illustrated) and an object 4 under examination, for example a patient, and strikes an arcuate detector 5. The detector 5 is a linear array formed by a row of detector elements. The X-ray source 1 and the detector 5 are mounted on a gantry 13 which is rotatable by a drive 14. The X-ray source 1 and the detector 5 thus form a measurement system which can be rotated around a system axis 6 which is at a right angle to the plane of the drawing in FIG. 1, with the result that the object 4 under examination is irradiated from different projection angles α. The detector elements of the detector 5 produce output signals from which a data acquisition system 7 forms measured values, referred to hereinafter as measured projections, which are fed to a computer 8.

A larger volume of the object 4 under examination can be scanned by the measurement system 1, 5 performing a spiral scan of the desired volume. In this case, a relative movement takes place between the measurement arrangement formed by the X-ray source 1 and the detector 5, and the object 4 under examination, in the direction of the system axis 6, which thus simultaneously represents the longitudinal axis of the spiral scan. This occurs preferably by displacement of a support device 10, provided for receiving the object 4 under examination, in the direction of the system axis 6.

A keyboard 12, which enables the CT device to be controlled, is connected to the computer 8, which, in the exemplary embodiment, is at the same time a control unit and performs the control of the CT device (it is also possible to provide a separate computer as a control unit).

The computer 8 also serves, in particular, to set the tube current, and hence the output power, of the X-ray source 1 supplied by a voltage generator 11.

Therefore the computer 8 is in control communication by any suitable means with the drive 14, the voltage generator 11, the support device 10, and the X-ray source 1. Moreover the X-ray source 1 includes, or has connected therewith, a diaphragm 1r for collimating (gating) the X-ray beam. The computer 8 also is in control communication with the diaphragm 15.

The irradiation from different projection angles α is is undertaken to obtain a number of measured projections. To that end, the X-ray source 1 irradiates the object 4 under examination with the X-ray beam 3 emitted at successive positions of the focus 2 which lie on the spiral track described by the focus 2, each position of the focus 2 being assigned to a projection angle and to a z-position on a z-axis corresponding to the system axis 6.

On account of the spiral scan, at most one measured projection can exist with respect to an image plane disposed at a right angle to the system axis 6, this measured projection being recorded with a position of the focus 2 lying in this image plane. In order nevertheless to be able to calculate a sectional image of that layer of the object 4 under examination which is associated with the respective image plane, calculated projections lying in the image plane thus have to be obtained by suitable interpolation methods from measured projections recorded in the vicinity of the image plane, and, as in the case of measured projections, each calculated projection is assigned to a projection angle α and to a z-position with respect to the system axis 6.

From the projections associated with a desired image plane, the computer 8 reconstructs a sectional image according to reconstruction algorithms known per se and represents them on a display unit 9, e.g. a monitor.

The keyboard 12 can be used to set operational parameters of the CT device, e.g.

Scan time, mAs product per sectional image, i.e. the product of that time in which the data on which the sectional image is based were obtained and the tube current I set during this time effective slice thickness, also referred to as reconstructed slice thickness, i.e. the extent measured in the direction of the system axis—of that region of the object under examination which contributes to the reconstructed image. As an example, the half-value width of the so-called slice sensitivity profile serves as a measure, collimated slice thickness, i.e. the extent—set by one or more diaphragms 15 and measured in the direction of the system axis—of an X-ray beam striking the linear array of detector elements, rotation time, i.e. the time that elapses during a complete revolution (360°) of the X-ray source, pitch (only for spiral scans), scan length, focus size, i.e. dimensions of the focal spot of the X-ray source 1 from which the X-rays emerge.

If an operator uses the keyboard 12 to enter a combination of operational parameters which is intended to form the basis for the performance of an examination, then this initially represents only a preliminary selection, because the computer 8 checks this combination of operational parameters before the performance of the examination to determine whether the combination might lead to an impermissible operating state of the CT device. To that end, the computer 8 takes the technical limits of the CT device into account as well as user-defined limits for individual operational parameters, which can likewise be entered via the keyboard 12. Values with respect to the technical limits of the CT device are stored in a memory associated with the computer 8.

If the computer 8 determines that a combination of operational parameters preselected using the keyboard 12 might lead to an impermissible operating state, then it determines, for at least one operational parameter, a value which deviates from the preselected combination of operational parameters and for which the planned examination can be carried out while avoiding the impermissible operating state without a significant reduction in the image quality, by comparison with the preselected combination of operational parameters.

In this connection, communication takes place between the user and the CT device via the keyboard 12 and the display unit 9. A combination of operational parameters with which the CT device finally performs the planned (user-intended) examination is defined during this communication. An additional display unit also may be provided for such communication, with the consequence that the display unit 9 is reserved solely for displaying the reconstructed sectional images.

The way in which this communication proceeds is explained below using the example of the two operational parameters tube current/and scan time T.

The thermal loading capacity of the X-ray source 1 can be described by the two operational parameters tube current I and scan time T. Depending on the thermal preloading and, if appropriate, depending on the focus size and tube voltage of the X-ray source 1 selected via the keyboard 12, the thermal loading capacity varies, which is determined by the computer 8 or a dedicated load computer, assigned to the X-ray source and communicating with the computer 8, taking account of the thermal preloading. The thermal loading capacity is represented as a function of the tube current I and the scan time T as a dashed curve 1 in FIG. 2 qualitatively on the basis of a specific preloading of the X-ray source 1. All scans with combinations of the operational parameters I and T which lie below the curve 1 can be carried out, whereas scans with combinations of the operational parameters I and T above the curve 1 would exceed the thermal loading capacity of the X-ray source 1. They thus lead to impermissible operating states for which reason they cannot, therefore, be performed and are blocked by the computer 8.

Generally, there is no mathematically simple relationship between the operational parameters I and T for a given loading capacity, in particular I·T=const. generally does not hold true. Thus, as an example, if the scan time is doubled for a specific thermal loading capacity, then the tube current generally need not be halved, but rather be reduced only by e.g. 20%.

The image quality, i.e. the image noise, of the sectional images generated is essentially determined by the mAs product, which contributes to a reconstructed sectional image. By changing the mAs product, with otherwise unchanged operational parameters and parameters of the image reconstruction algorithm, the noise in the sectional image is changed, while the same mAs product yields at least essentially the same noise and thus approximately the same image quality.

The computer 8 of the CT device according to the invention calculates, on the basis of the data obtained during a spiral scan, sectional images by means of an image reconstruction algorithm in which the layer sensitivity profile of a reconstructed sectional image does not depend significantly on the pitch, whereas the mAs product contributing to the sectional image is dependent on the pitch. In such an image reconstruction algorithm, for each projection angle all the measured values associated with this projection angle which lie within a maximum distance from the image plane are incorporated in the reconstruction in a weighted manner. The weighting is according to their spatial distance in the direction of the longitudinal axis of the spiral scanning from the image plane in accordance with a weighting function. The weighting function is chosen such that the slice thickness is essentially independent of the pitch.

Consequently, the following relationship holds true:

$$I \propto mAs \cdot p = \frac{mAs \cdot L \cdot ROT}{coll \cdot T} \quad \text{(Equation 1)}$$

In this case:
I: denotes the tube current
P: denotes the pitch
L: denotes the scan length
ROT: denotes the rotation time
coll: denotes the collimated slice thickness
T: denotes the scan type.

It is clear from Equation 1 that the mAs product contributing to a reconstructed sectional image is proportional to the product I·T of tube current and scan time. Thus, in the reconstruction algorithm employed, the image quality only depends on the product I·T if the other parameters (collimated coll and reconstructed layer thickness, scan length L and rotation time ROT) are not changed. However, image artifacts may increase appreciably in the case of large values of the pitch p.

Figure 2:
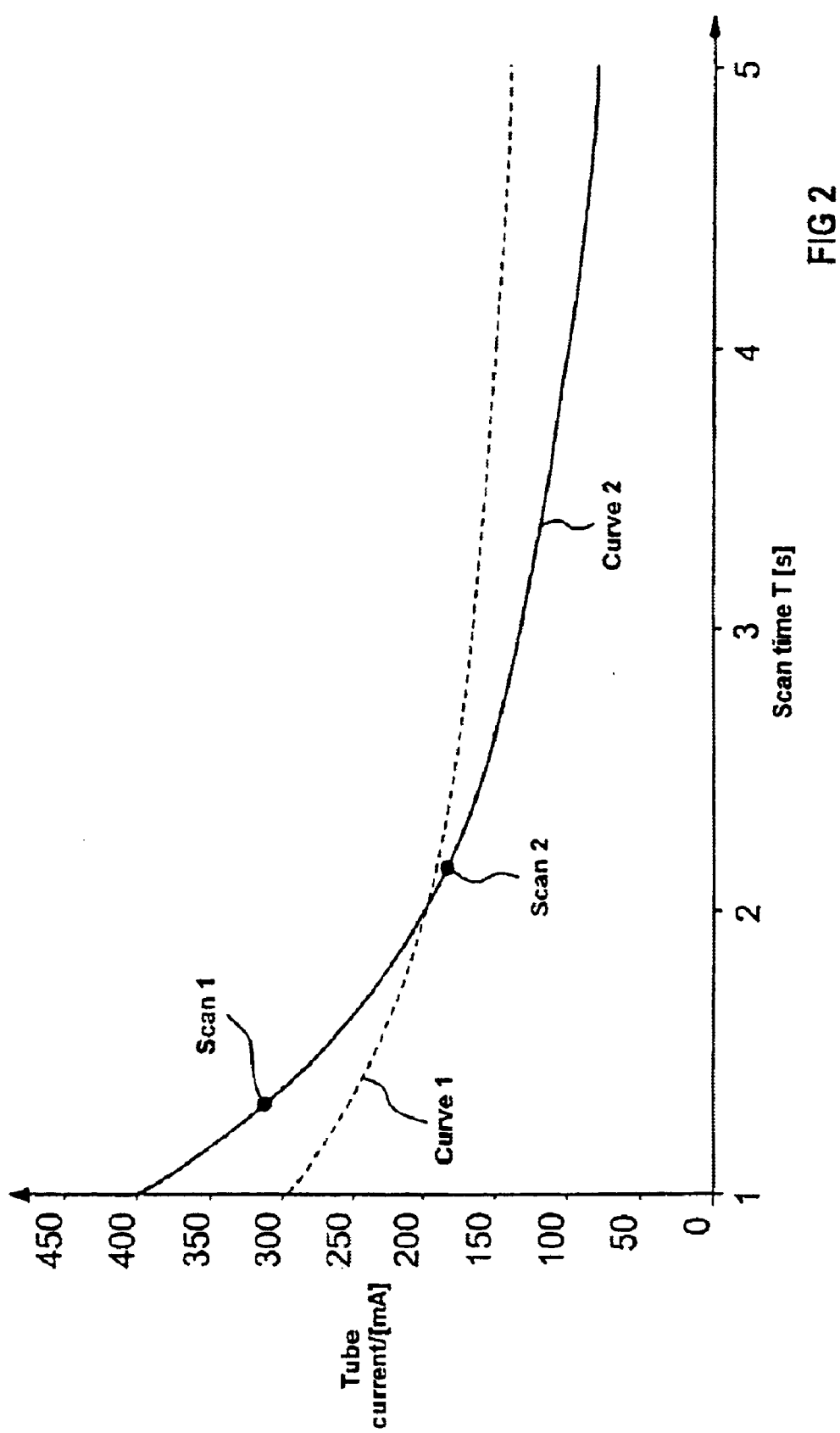
FIG. 2 shows the relationship between the tube current and the scan time for assistance in explaining the operation of the inventive computed tomography apparatus.

FIG. 2 additionally illustrates a solid curve—designated by curve 2—of constant image quality, for which I·T=const. holds true, with the consequence that, for a sectional image generated with values corresponding to a point on the curve 2, a constant mAs product which is independent of the position of the point on the curve 2 is used, thereby achieving a constant image noise and hence a constant image quality.

Generally, one part of the curve 2 lies above the permissible thermal loading of the X-ray source 1 in accordance with curve 1, and another part lies below it. If as an example a scan—designated by scan 1—is considered with a combination of the operational parameters I and T above curve 1, this scan would be impermissible on account of excessively high thermal loading of the X-ray source 1. The properties of the abovementioned reconstruction algorithm allow the combination of the operational parameters I and T to be changed, without any loss in image quality, to the extent that the permissible thermal loading in accordance with curve 1 is no longer exceeded. The corresponding combination of the operational parameters I and T is designated by scan 2. In the case illustrated, the tube current I is reduced and the scan time T is simultaneously lengthened, the operational parameters for scan 2 being chosen whilst taking account of curve 1 such that they are as close as possible to the originally preselected operational parameters in accordance with scan 1. The reduction in the pitch p accompanying the lengthened scan time T does not lead to a significant change in the layer sensitivity profile on account of the reconstruction algorithm used.

The changing of the operational parameters so that the loading capacity of the CT system is no longer exceeded, without degrading the image quality, can either be carried out automatically by the computer 8 (with or without a corresponding indication to the user displayed on the display unit 9 by the computer 8) or can be presented to the user as a proposal by the computer 8, in which case the computer 8 displays a possible indication or a proposal, in the exemplary embodiment, on the display unit 9 and a proposal can be adopted by the user through corresponding actuation of the keyboard 12.

Changes in the operational parameters are possible only within the technical limits of the device. Technical limits may include, in addition to the thermal loading capacity of the X-ray source, inter alia: maximum and minimum tube current that can be set, maximum and minimum pitch that can be set, maximum and minimum scan time that can be set.

In the case of the reconstruction algorithms known as 180° LI and 360° LI interpolation algorithms, the procedure described with regard to the setting of the tube current I and the scan time T is not possible since, in the case of these algorithms, the layer sensitivity profile is dependent on the pitch p, whereas the mAs product is independent of the pitch p.

Within the technical limits of the CT device, by means of the keyboard 12, the user can additionally set user-defined limit values with regard to the operational parameters within which a change in the respective operational parameter is only possible in that case: thus, as an example, it is possible to define a maximum permissible scan time in order to be able to carry out the scan e.g. while holding one's breath. Equally, it is possible to define a maximum permissible pitch in order e.g. to limit the artifact intensity. Finally, it is possible to define a minimum pitch in order e.g. not to fall below a specific temporal resolution.

These user-defined limits either cannot be exceeded at all, or can only be exceeded after confirmation of an indication in this respect which is displayed on the display unit 9 by the computer, by corresponding actuation of the keyboard 12.

Instead of exceeding the technical or user-defined limits, the computer 8 can perform a change in operational parameters other than those (I, T) mentioned above, in order to enable a desired scan. Thus, as an example, it is possible to change the mAs product contributing to the reconstructed sectional image, the effective slice thickness, the focus size, the rotation time or the waiting time that influences the thermal loading capacity and hence the maximum permissible scan time, before the scan. Such changes can again be effected automatically or performed by the computer 8 only after confirmation of an indication in this respect which is displayed on the display unit 9 by the computer 8, by corresponding actuation of the keyboard 12.

It is also possible to change a number of operating parameters in order to enable a desired scan. In this case, protocols concerning the order in which the individual operational parameters are to be changed are stored in the computer B, for example in the memory provided for the technical limit values of the CT device. As an alternative, said order may be influenced or determined by the user by means of the keyboard 12.

Thus, it may be expedient, for example in the event of excessively high loading, for the computer 8 to first reduce the tube current I while simultaneously lengthening the scan time. If the scan time reaches a maximum permissible scan time before the loading falls below the permissible thermal loading of the X-ray source 1, then the computer 8, in order to enable the scan, switches e.g. to a larger focus of the X-ray source 1. If this still does not suffice to bring about a permissible operating state, the computer 8 may additionally reduce e.g. the mAs product.

Figure 3:
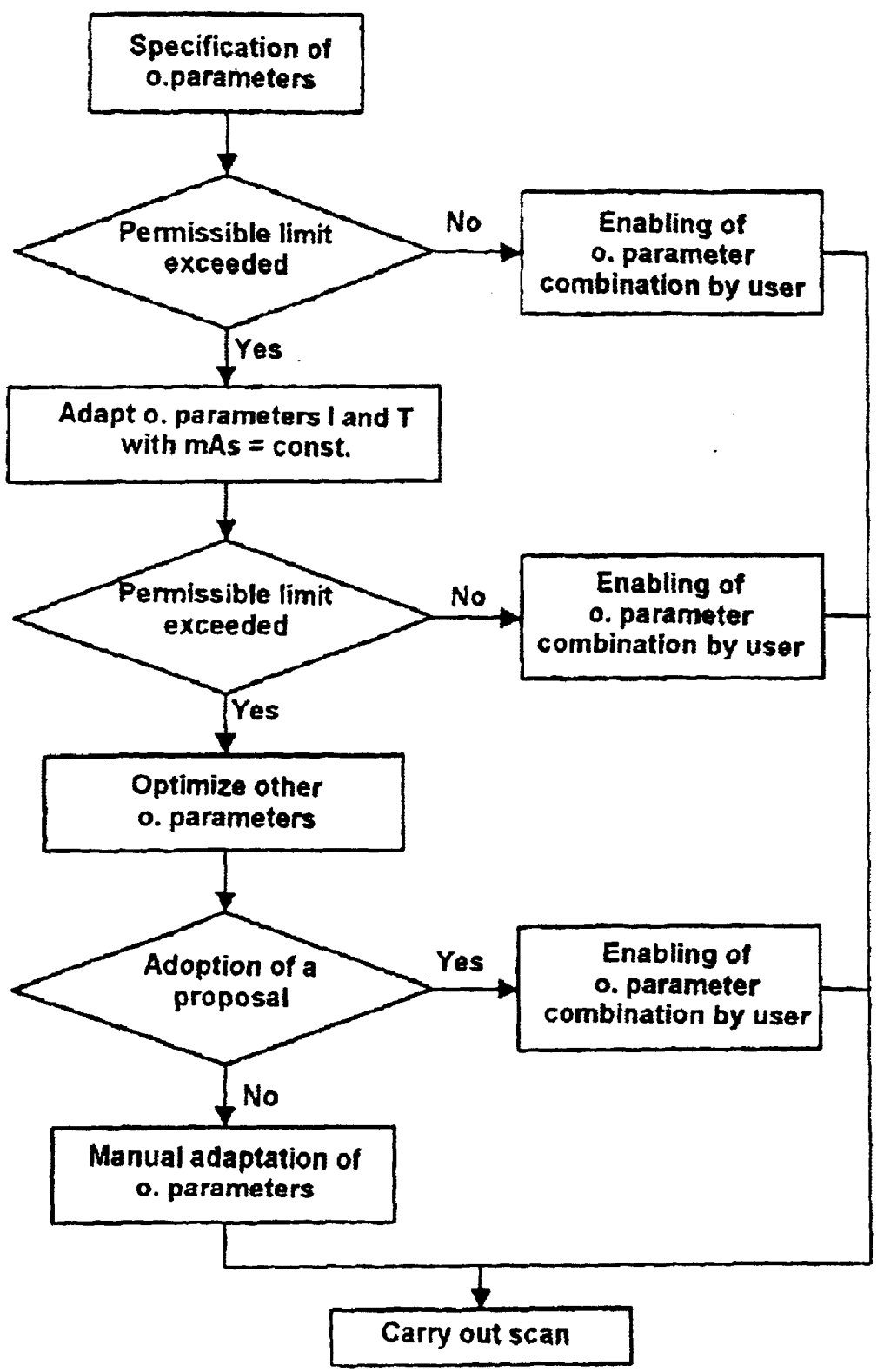
FIG. 3 is a flow chart illustrating the operation of the computed tomography apparatus in accordance with the invention.

FIG. 3 diagrammatically illustrates the described method of operation of a CT device according to the invention in the form of a flow diagram, to be precise for the case where changes of operational parameters require enabling by the user. In this case, O. parameters denotes operational parameters in FIG. 3. The term "permissible limit" encompasses both technical limits of the CT device and limit values defined by the user within these limits.

The stepwise procedure already described above is described, according to which, in the case of a limit being exceeded, firstly a change is made to the operational parameters tube current I and scan time T under the condition mAs=const., and, if this change does not suffice, other operational parameters are optimized while taking account of the limits. If a useable combination of operational parameters cannot be realized in this way, then it becomes clear from FIG. 3 that it is then incumbent upon the user to manually adapt operational parameters in order to bring about a situation which enables a scan to be carried out.

The method of operation of the CT device according to the invention was described above for the case where a single scan is to be effected. However, it applies equally to cases in which a sequence of scans is to be performed, whether with the scans directly succeeding one another, or with the scans being separated from one another by time intervals.

The invention, though this is particularly advantageous, is not restricted to the exemplary embodiment of spiral scans on the basis of a reconstruction algorithm in which the slice sensitivity profile of a reconstructed sectional image does not depend significantly on the pitch, whereas the mAs product contributing to the sectional image is dependent on the pitch. The invention also can be employed in conjunction with any other type of scan which does not involve spiral scans, for example, individual planar scans or sequences of planar scans (sequential scan).

In the exemplary embodiment a CT device with a detector having a single linear array of detector elements is described. However, the invention is not restricted to CT devices with such detectors, but rather also encompasses CT devices with detectors having a number of linear arrays of detector elements (multi-linear-array detectors) and also CT devices with detectors having a multiplicity of detector elements arranged in a(matrix array detector).

The invention was explained above using the example of a third-generation CT device. However, it can also be employed in fourth-generation CT devices which, instead of an arcuate detector that can be adjusted with the X-ray source about the system axis, has a stationary ring of detector elements.

The invention can be used both in the medical field and in non-medical fields.

What is claimed is:

1. A computed tomography apparatus comprising:

a measurement unit adapted to receive an examination subject, said measurement unit, in a scan of said subject, generating data values for said subject;

a control unit connected to said measurement unit for operating said measurement unit during said scan according to a combination of operating parameters;

an image computer supplied with said data values for reconstructing an image of said subject from said data values, said image having an image quality;

a user-operable input unit connected to said control unit allowing a user to enter a selected combination of said operating parameters for conducting a user-intended scan, said selected combination, if implemented, causing an image with a user-intended image quality to be reconstructed; and said control unit determining whether said selected combination would produce an impermissible operating state of said measurement unit and, if so, said control unit causing at least one of said operating parameters in said selected combination to be altered to a value which permits said user-intended scan to be conducted while avoiding said impermissible operating state and which produces an image of said subject having an image quality which is not significantly reduced in comparison to said user-intended image quality.

2. A computed tomography apparatus as claimed in claim 1 wherein said control unit automatically sets said altered value of said at least one of said operating parameters in said selected combination, and automatically operates said measurement unit to conduct said scan with said altered value.

3. A computed tomography apparatus as claimed in claim 2 wherein said control unit generates information identifying said altered value which has automatically been set.

4. A computed tomography apparatus as claimed in claim 1 wherein said control unit generates information identifying said altered value, and wherein said control unit must be enabled, by an input entered via said input unit, to conduct said user-intended scan with said altered value.

5. A computed tomography apparatus as claimed in claim 1 wherein said measurement unit is adapted for conducting a spiral scan of said subject, and wherein said measurement unit includes an X-ray source which emits an X-ray beam, a radiation detector disposed in said X-ray beam, and a subject support adapted to receive said subject thereon, said measurement unit rotating said X-ray source and said radiation detector around said subject while effecting a relative longitudinal movement between said X-ray source and said detector, and said subject support, said measurement unit conducting said spiral scan with a defined effective slice thickness during a scan time during which the X-ray source is operated with a tube current, and wherein said control unit, to avoid said impermissible operating state, alters said at least one of said operating parameters in said selected combination so that an mAs product contributing to a sectional image of the defined effective slice thickness is not significantly reduced in comparison to an mAs product contributing to said sectional image of said defined effective slice thickness in said user-intended scan.

6. A computed tomography apparatus as claimed in claim 5 wherein said spiral scan has a pitch associated therewith, and wherein said image computer reconstructs a sectional image of said subject so that a layer sensitivity profile of the reconstructed sectional image is substantially independent of the pitch, with the mAs product, employed for obtaining the data values from which said reconstructed sectional image is reconstructed, is dependent on the pitch.

7. A computed tomography apparatus as claimed in claim 6 wherein said operating parameters include said scan time and said tube current, and wherein said control unit keeps the product of said tube current and said scan time, in the scan conducted with said altered value, equal to the product of the tube current and the scan time in said selected combination.

8. A computed tomography apparatus as claimed in claim 6 wherein said X-ray source has a focus, with a focus size, from which said X-ray beam is emitted, and further comprising a beam diaphragm for gating said X-ray beam to produce a collimated slice thickness, and wherein said input unit allows entry of at least one of an upper limit value and a lower limit value for at least one operating parameter selected from the group consisting of maximum permissible scan time, minimum mAs product per sectional image, maximum mAs product per sectional image, minimum effective slice thickness, maximum effective slice thickness, minimum collimated slice thickness, maximum collimated slice thickness, minimum rotation time, maximum rotation time, minimum pitch, maximum pitch, minimum scan length, maximum scan length, minimum waiting time before conducting said scan, maximum waiting time before conducting said scan, and focus size.

9. A computed tomography apparatus as claimed in claim 8 wherein said control unit optimizes the operating parameters in said selected combination relative to at least one optimization goal, dependent on said at least one of said upper limit and said lower limit.

10. A computed tomography apparatus as claimed in claim 9 wherein said control unit optimizes the operating parameters in said selected combination relative to an optimization goal selected from the group consisting of minimum scan time, maximum spatial resolution, maximum temporal resolution, and maximum scan length.

11. A computed tomography apparatus as claimed in claim 9 wherein said control unit optimizes said operating parameters of said selected combination dependent on a plurality of optimization goals, and wherein said control unit ranks the respective optimization goals in said plurality of optimization goals dependent on ranks entered via said input unit.

12. A computed tomography apparatus as claimed in claim 8 wherein said control unit determines whether it is impossible to avoid an impermissible operating state and to comply with said at least one of said upper limit value and said lower limit value and wherein, if compliance is impossible, said control unit makes available a combination of operating parameters which approximate said selected combination without producing an impermissible operating state of said measurement unit.

13. A computed tomography apparatus as claimed in claim 12 wherein, if compliance is impossible, said control unit makes available a plurality of combinations of operating parameters, said combinations being respectively optimized dependent on different optimization goals.

14. A computed tomography apparatus as claimed in claim 12 wherein said control unit automatically operates said measurement unit to conduct said user-intended scan with said combination of operating values which approximates said selected combination.

15. A computed tomography apparatus as claimed in claim 14 wherein said control unit makes information available identifying each value of each operating parameter in said combination of operating parameters which approximates said selected combination, which does not comply with said at least one of said upper limit value and said lower limit value.

16. A computed tomography apparatus as claimed in claim 12 wherein said control unit makes information available identifying any value of any of said operating parameters in said combination of operating parameters which approximates said selected combination, which does not comply with said at least one of said upper limit value and said lower limit value, and wherein said control unit requires enablement, via said input unit, to conduct said user-intended scan using said combination of operating values which approximates said selected combination.

17. A computed tomography apparatus as claimed in claim 1 wherein said control unit generates and makes available a plurality of different combinations of operating parameters, for successive scans of said subject, respectively dependent on different optimization goals for optimizing said operating parameters.

18. A computed tomography apparatus as claimed in claim 1 wherein said control unit ranks said operating parameters dependent on a rank order entered via said input unit, and selects an operating parameter for alteration dependent on its rank order.

19. A computed tomography apparatus as claimed in claim 1 wherein said measurement unit has an X-ray source which emits an X-ray beam from a focus having a focus size, and a radiation detector on which said X-ray beam is incident with an effective slice thickness, and a beam diaphragm disposed for gating said X-ray beam to produce a collimated slice thickness, said X-ray source and said radiation detector being rotatable around said subject to conduct said scan, and wherein said image computer reconstructs a sectional image of said subject, the data values used by said image computer to reconstruct said sectional image having been produced by said measurement unit with an mAs product, and wherein said input unit allows entry of at least one of an upper limit value and a lower limit value for at least one operating parameter selected from the group consisting of maximum permissible scan time, minimum mAs product per sectional image, maximum mAs product per sectional image, minimum effective slice thickness, maximum effective slice thickness, minimum collimated slice thickness, maximum collimated slice thickness, minimum rotation time, maximum rotation time, minimum scan length, maximum scan length, minimum waiting time before conducting said scan, maximum waiting time before conducting said scan and focus size.

20. A computed tomography apparatus as claimed in claim 19 wherein said control unit optimizes the operating parameters in said selected combination relative to at least one optimization goal, dependent on said at least one of said upper limit and said lower limit.

21. A computed tomography apparatus as claimed in claim 20 wherein said control unit optimizes the operating parameters in said selected combination relative to an optimization goal selected from the group consisting of minimum scan time, maximum spatial resolution, maximum temporal resolution, and maximum scan length.

22. A computed tomography apparatus as claimed in claim 20 wherein said control unit optimizes said operating parameters of said selected combination dependent on a plurality of optimization goals, and wherein said control unit ranks the respective optimization goals in said plurality of optimization goals dependent on ranks entered via said input unit.

23. A computed tomography apparatus as claimed in claim 19 wherein said control unit determines whether it is impossible to avoid an impermissible operating state and to comply with said at least one of said upper limit value and said lower limit value and wherein, if compliance is impossible, said control unit makes available a combination of operating parameters which approximate said selected combination without producing an impermissible operating state of said measurement unit.

24. A computed tomography apparatus as claimed in claim 23 wherein, if compliance is impossible, said control unit makes available a plurality of combinations of operating parameters, said combinations being respectively optimized dependent on different optimization goals.

25. A computed tomography apparatus as claimed in claim 23 wherein said control unit automatically operates said measurement unit to conduct said user-intended scan with said combination of operating values which approximates said selected combination.

26. A computed tomography apparatus as claimed in claim 25 wherein said control unit makes information available identifying each value of each operating parameter in said combination of operating parameters which approximates said selected combination, which does not comply with said at least one of said upper limit value and said lower limit value.

27. A computed tomography apparatus as claimed in claim 23 wherein said control unit makes information available identifying any value of any of said operating parameters in said combination of operating parameters which approximates said selected combination, which does not comply with said at least one of said upper limit value and said lower limit value, and wherein said control unit requires enablement, via said input unit, to conduct said user-intended scan using said combination of operating values which approximates said selected combination.

\* \* \* \* \*